(12) United States Patent
Urchuk

(10) Patent No.: US 11,039,808 B2
(45) Date of Patent: Jun. 22, 2021

(54) SCANNING SYSTEMS CONFIGURED TO INSPECT CONVEYED OBJECTS AND RELATED SYSTEMS AND METHODS

(71) Applicant: Analogic Corporation, Peabody, MA (US)

(72) Inventor: Steven N. Urchuk, Melrose, MA (US)

(73) Assignee: Analogic Corporation, Peabody, MA (US)

( * ) Notice: Subject to any disclaimer, the term of this patent is extended or adjusted under 35 U.S.C. 154(b) by 0 days.

(21) Appl. No.: 16/275,103

(22) Filed: Feb. 13, 2019

(65) Prior Publication Data
US 2020/0253576 A1 Aug. 13, 2020

(51) Int. Cl.
*A61B 6/00* (2006.01)
(52) U.S. Cl.
CPC .............. *A61B 6/54* (2013.01); *A61B 6/4476* (2013.01); *A61B 6/5205* (2013.01)
(58) Field of Classification Search
CPC ...... G01N 23/02; G01N 23/185; G01V 5/005; G01V 5/0066; A61B 6/54; A61B 6/4476
USPC .......................................................... 378/57
See application file for complete search history.

(56) References Cited

U.S. PATENT DOCUMENTS

| | | | | |
|---|---|---|---|---|
| 3,288,038 A | * | 11/1966 | Swartz | B65H 29/60 414/788.9 |
| 3,862,400 A | * | 1/1975 | Thomson | G07G 1/10 235/462.28 |
| 3,952,195 A | * | 4/1976 | Heisner | G01N 23/083 378/61 |
| 4,330,061 A | * | 5/1982 | Rudszinat | B07C 5/362 209/3.1 |
| 6,185,272 B1 | * | 2/2001 | Hiraoglu | G01V 5/0008 378/57 |
| 6,721,387 B1 | | 4/2004 | Naidu et al. | |
| 6,813,374 B1 | * | 11/2004 | Karimi | G06K 9/00771 378/207 |
| 7,724,866 B2 | | 5/2010 | Naidu et al. | |

(Continued)

OTHER PUBLICATIONS

International Search Report for International Application No. PCT/US2020/016433, dated Jun. 19, 2020, 2 pages.

(Continued)

*Primary Examiner* — Dani Fox
(74) *Attorney, Agent, or Firm* — TraskBritt

(57) ABSTRACT

Scanning systems for performing computed tomography scanning may include a stator, a rotor supporting at least one radiation source and at least one radiation detector rotatable with the rotor, and a rotator operatively connected to the rotor to rotate the rotor relative to the stator. A conveyor system may include a respective conveyor extending through the rotor of the scanning system. A control system operatively connected to the scanning system and the conveyor system may be configured to automatically and dynamically increase a rate at which the rotor moves, decrease a rate at which the respective conveyor moves, and/or adjust other system parameters when the control system enters a finer pitch mode and to automatically and dynamically decrease a rate at which the rotor moves, increase a rate at which the respective conveyor moves, and/or adjust other system parameters when the control system enters a coarser pitch mode.

19 Claims, 8 Drawing Sheets

(56) References Cited

U.S. PATENT DOCUMENTS

| | | | | |
|---|---|---|---|---|
| 8,598,819 B2* | 12/2013 | Rollman | | H02P 29/02 |
| | | | | 318/376 |
| 8,781,062 B2 | 7/2014 | Besson | | |
| 9,121,957 B2 | 9/2015 | Naidu et al. | | |
| 9,853,694 B2 | 12/2017 | Sloutsky et al. | | |
| 2005/0031069 A1* | 2/2005 | Kaucic | | G01V 5/0016 |
| | | | | 378/19 |
| 2005/0111619 A1* | 5/2005 | Bijjani | | G01V 5/005 |
| | | | | 378/57 |
| 2005/0226360 A1* | 10/2005 | Kaucic, Jr. | | G01N 23/046 |
| | | | | 378/4 |
| 2005/0276376 A1* | 12/2005 | Eilbert | | A61B 6/482 |
| | | | | 378/57 |
| 2007/0172026 A1* | 7/2007 | Schlomka | | A61B 6/482 |
| | | | | 378/19 |
| 2007/0230657 A1* | 10/2007 | Garms | | G01V 5/005 |
| | | | | 378/57 |
| 2009/0003515 A1* | 1/2009 | Naidu | | G01T 1/2985 |
| | | | | 378/14 |
| 2010/0171255 A1* | 7/2010 | Gulbrandsen | | B65H 5/26 |
| | | | | 270/52.19 |
| 2010/0277312 A1* | 11/2010 | Edic | | G01V 5/005 |
| | | | | 340/540 |
| 2011/0002440 A1* | 1/2011 | Gatten | | G01V 5/005 |
| | | | | 378/19 |
| 2011/0211666 A1* | 9/2011 | Ying | | A61B 6/032 |
| | | | | 378/9 |
| 2011/0228896 A1* | 9/2011 | Peschmann | | G01V 5/0091 |
| | | | | 378/5 |
| 2011/0317807 A1* | 12/2011 | Gatten | | G01V 5/005 |
| | | | | 378/20 |
| 2012/0069964 A1* | 3/2012 | Scrolling | | G01N 23/20083 |
| | | | | 378/97 |
| 2012/0294415 A1* | 11/2012 | Roshi | | A61B 6/032 |
| | | | | 378/16 |
| 2013/0156156 A1* | 6/2013 | Roe | | G01V 5/0033 |
| | | | | 378/57 |
| 2015/0054435 A1* | 2/2015 | Silitonga | | H02P 7/2815 |
| | | | | 318/400.04 |
| 2015/0177165 A1* | 6/2015 | Ying | | A61B 6/027 |
| | | | | 378/9 |
| 2017/0059496 A1* | 3/2017 | Shaughnessy | | G01M 17/028 |
| 2017/0184757 A1* | 6/2017 | Miao | | G01V 5/0041 |
| 2019/0156472 A1* | 5/2019 | Link | | G06K 9/6202 |

OTHER PUBLICATIONS

International Written Opinion for International Application No. PCT/US2020/016433, dated Jun. 19, 2020, 11 pages.

* cited by examiner

SCANNING SYSTEMS CONFIGURED TO INSPECT CONVEYED OBJECTS AND RELATED SYSTEMS AND METHODS

FIELD

This disclosure relates generally to scanning systems configured to perform computed tomography and methods of operating scanning systems configured to perform computed tomography. More specifically, disclosed embodiments relate to scanning systems configured to inspect conveyed objects using computed tomography that may automatically and dynamically adjust operating parameters to better meet shifting priorities in response to real-time updates.

BACKGROUND

When performing computed tomography (CT) scanning of objects, constant pitch helical cone beam techniques may be used for most applications. For example, the ratio of the rate of linear displacement of a conveyor or table for supporting objects to be scanned per gantry rotation to the size of the detector array along the direction of conveyor or table movement may remain at least substantially constant. More specifically, the actual rate of linear displacement of the conveyor or table and the actual rate of rotational displacement of the gantry may be at least substantially fixed.

As one application, CT-based explosive detection systems for checked baggage screening generally use a constant pitch. When a line scanner is used for pre-screening followed by a CT scanner in carry-on baggage screening, the belt speed of the system may be manually varied to carry the bag to the exit of the scanner without further examination following an initial clearance and may manually return the CT scanner returns to its normal speed to scan the bag, reconstruct CT images, and perform threat detection on the bag following an initial failure to clear. U.S. Pat. No. 7,724,866, issued May 25, 2010, and assigned to the same assignee as this application, discloses image processing techniques that may account for these changes in pitch to produce quality images from the scanned data.

BRIEF SUMMARY

In some embodiments, scanning systems may include at least one scanning system configured to perform computed tomography scanning. Each scanning system may include a stator, a rotor supporting at least one radiation source and at least one radiation detector rotatable with the rotor, and a rotator operatively connected to the rotor to rotate the rotor relative to the stator. A conveyor system may include a respective conveyor extending through the rotor of each scanning system. A control system operatively connected to the scanning system and the conveyor system may be configured to automatically and dynamically increase a rate at which the rotor moves, decrease a rate at which the respective conveyor moves, and/or adjust other system parameters when the control system enters a finer pitch mode. The control system may also automatically and dynamically decrease a rate at which the rotor moves, increase a rate at which the respective conveyor moves, and/or adjust other system parameters when the control system enters a coarser pitch mode.

In other embodiments, assemblies of scanning systems may include a first group of scanning systems configured to perform computed tomography scanning at a first pitch and a second group of scanning systems configured to perform computed tomography scanning at a second, finer pitch. Each of the first and second groups of scanning systems may include at least one scanning system including a stator and a rotor. The rotor may support at least one radiation source and at least one radiation detector rotatable with the rotor. A rotator may be operatively connected to the rotor to rotate the rotor. A conveyor system may include an input conveyor, a respective conveyor operatively connected of the input conveyor and extending through the rotor of each scanning system, and an output conveyor operatively connected to each respective conveyor. A control system operatively connected to the scanning system and the conveyor system may be configured to automatically and dynamically assign at least one scanning system from the first group of scanning systems to the second group of scanning systems, causing the at least one scanning system to increase a rate at which the rotor moves, decrease a rate at which the respective conveyor moves, and/or adjust other system parameters to increase scan quality. The control system may also to automatically and dynamically assign at least another scanning system from the second group of scanning systems to the first group of scanning systems, causing the at least another scanning system to hold a rate at which the rotor moves, increase a rate at which the respective conveyor moves, and/or adjust other system parameters to increase throughput.

In other embodiments, methods of operating scanning systems may involve scanning a first object in a first, finer pitch mode utilizing a scanning system configured to perform computed tomography scanning by rotating a rotor supporting at least one radiation source and at least one radiation detector rotatable with the rotor relative to a stator at a first rotational rate utilizing a rotator operatively connected to the rotor and causing a conveyor extending through the rotor of the scanning system to move the first object past the at least one radiation source and the at least one radiation detector at a first linear rate. The scanning system may switch from the first, finer pitch mode to a second, coarser pitch mode utilizing a control system operatively connected to the scanning system and the conveyor by rotating the rotor at a second, slower rotational rate utilizing the rotator, causing the conveyor to move at a second, faster linear rate, or both. A second, different object may be scanned in the second, coarser pitch mode by rotating the rotor at the second, slower rotational rate utilizing the rotator, causing the conveyor to move the second object past the at least one radiation source and the at least one radiation detector at the second, faster linear rate, or both.

In other embodiments, computer-readable media may include computer-executable instructions, which when executed cause a control system for a scanning system to: scan a first object in a first, finer pitch mode utilizing a scanning system configured to perform computed tomography scanning by rotating a rotor supporting at least one radiation source and at least one radiation detector rotatable with the rotor relative to a stator at a first rotational rate utilizing a rotator operatively connected to the rotor and causing a conveyor extending through the rotor of the scanning system to move the first object past the at least one radiation source and the at least one radiation detector at a first linear rate. The instructions may further cause the scanning system to switch from the first, finer pitch mode to a second, coarser pitch mode by rotating the rotor at a second, slower rotational rate utilizing the rotator, causing the conveyor to move at a second, faster linear rate, or both.

The instructions may cause the scanning system to scan a second, different object in the second, coarser pitch mode by rotating the rotor at the second, slower rotational rate utilizing the rotator, causing the conveyor to move the second object past the at least one radiation source and the at least one radiation detector at the second, faster linear rate, or both.

BRIEF DESCRIPTION OF THE DRAWINGS

While this disclosure concludes with claims particularly pointing out and distinctly claiming specific embodiments, various features and advantages of embodiments within the scope of this disclosure may be more readily ascertained from the following description when read in conjunction with the accompanying drawings, in which:

DETAILED DESCRIPTION

The illustrations presented in this disclosure are not meant to be actual views of any particular assembly of scanning systems for performing computed tomography (CT) scanning or component thereof, but are merely idealized representations employed to describe illustrative embodiments. Thus, the drawings are not necessarily to scale.

Disclosed embodiments relate generally to scanning systems configured to perform CT scanning that may automatically and dynamically adjust operating parameters to better meet shifting priorities in response to real-time updates. More specifically, disclosed are embodiments of scanning systems configured to perform CT scanning that may automatically and dynamically adjust conveyor speed, gantry rotational rate, or both to adjust resulting image resolution in real-time in response to real-world factors impacting the likelihood that dangerous items may be identified.

As used herein, the terms "substantially" and "about" in reference to a given parameter, property, or condition means and includes to a degree that one of ordinary skill in the art would understand that the given parameter, property, or condition is met with a degree of variance, such as within acceptable manufacturing tolerances. For example, a parameter that is substantially or about a specified value may be at least about 90% the specified value, at least about 95% the specified value, at least about 99% the specified value, or even at least about 99.9% the specified value.

As used herein, spatially relative terms, such as "upper," "lower," "bottom," and "top," are for ease of description in identifying one element's relationship to another element, as illustrated in the figures. Unless otherwise specified, the spatially relative terms are intended to encompass different orientations of the materials in addition to the orientation depicted in the figures. Thus, the term "upper" can encompass elements above, below, to the left of, or to the right of other elements, depending on the orientation of a device. The materials may be otherwise oriented (rotated ninety degrees, inverted, etc.) and the spatially relative descriptors used herein interpreted accordingly.

Figure 1:
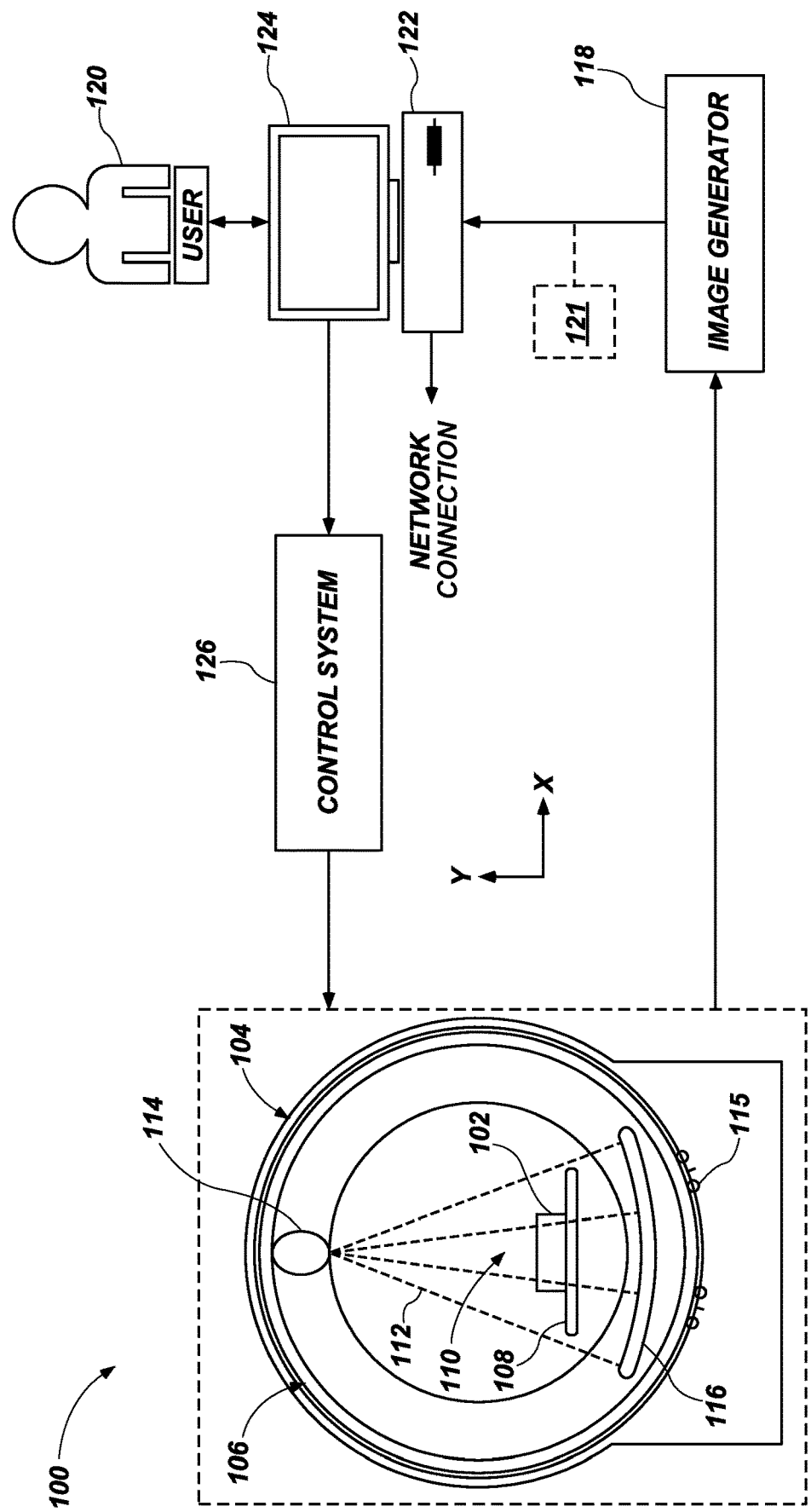
FIG. 1 is a schematic of a scanning system configured to perform computed tomography (CT) scanning.

FIG. 1 is a schematic of a scanning system 100 configured to perform CT scanning. Techniques in accordance with this disclosure may find applicability with, for example, CT systems, line-scan systems, digital projection systems, diffraction systems, and/or other systems comprising a radiation detector system. The scanning system 100 may be configured to examine one or more objects 102 (e.g., a series of suitcases at an airport, freight, parcels, etc.). The scanning system 100 may include, for example, a stator 104 and a rotor 106 rotatable relative to the stator 104. During examination, the object(s) 102 may be located on a support 108, such as, for example, a bed or conveyor belt, that is selectively positioned in an examination region 110 (e.g., a hollow bore in the rotor 106 in which the object(s) 102 is exposed to radiation 112), and the rotor 106 may be rotated about the object(s) 102 by a rotator 115 (e.g., motor, drive shaft, chain, etc.).

The rotor 106 may surround a portion of the examination region 110 and may be configured as, for example, a gantry supporting at least one radiation source 114 (e.g., an ionizing x-ray source, gamma-ray source, etc.) oriented to emit radiation toward the examination region 110 and at least one radiation detector 116 supported on a substantially diametrically opposite side of the rotor 106 relative to the radiation source(s) 114. During an examination of the object(s) 102, the radiation source(s) 114 emits fan and/or cone shaped radiation 112 configurations into the examination region 110. The radiation 112 can be emitted, for example at least substantially continuously or intermittently (e.g., a pulse of radiation 112 followed by a resting period during which the radiation source(s) 114 is not activated).

As the emitted radiation 112 traverses the object(s) 102, the radiation 112 may be attenuated differently by different aspects of the object(s) 102. Because different aspects attenuate different percentages of the radiation 112, an image or images can be generated based upon the attenuation, or variations in the number of radiation photons that are detected by the radiation detector 116. For example, more dense aspects of the object(s) 102, such as an inorganic material, may attenuate more of the radiation 112 (e.g., causing fewer photons to be detected by the radiation detector 116) than less dense aspects, such as organic materials.

The radiation detector 116 may include, for example, many individual detector elements arranged in a pattern (e.g., a row or an array) on one or more detection assemblies (also referred to as detection modules, detector modules, and/or the like), which are operatively connected to one another to form the radiation detector 116. In some embodiments, the detector elements may be configured to indirectly convert (e.g., using a scintillator array and photodetectors) detected radiation into analog signals. Further, as will be described in more detail below, the radiation detector 116, or detection assemblies thereof, may comprise electronic circuitry, such as, for example, an analog-to-digital (A/D) converter, configured to filter the analog signals, digitize the analog signals, and/or otherwise process the analog signals and/or digital signals generated thereby. Digital signals output from the electronic circuitry may be conveyed from the radiation detector 116 to digital processing components configured to store data associated with the digital signals and/or further process the digital signals.

In some embodiments, the digital signals may be transmitted to an image generator 118 configured to generate image space data, also referred to as images, from the digital signals using a suitable analytical, iterative, and/or other reconstruction technique (e.g., backprojection reconstruction, tomosynthesis reconstruction, iterative reconstruction, etc.). In this way, the data may be converted from projection space to image space, a domain that may be more understandable by a user 120 viewing the image(s), for example. Such image space data may depict a two dimensional representation of the object(s) 102 and/or a three dimensional representation of the object(s) 102. In other embodiments, the digital signals may be transmitted to other digital processing components, such as a threat analysis component 121, for processing.

The illustrated scanning system 100 may also include a terminal 122 (e.g., a workstation or other computing device), configured to receive the image(s), which can be displayed on a monitor 124 to the user 120 (e.g., security personnel, medical personnel, etc.). In this way, a user 120 can inspect the image(s) to identify areas of interest within the object(s) 102. The terminal 122 may also be configured to receive user input which may direct operations of the scanning system 100 (e.g., a rate at which the support 108 moves, activation of the radiation source(s) 114, etc.) and connected to additional terminals 122 through a network (e.g., a local area network or the Internet).

A control system 126 may be operably coupled to the terminal 122. The control system 126 may be configured to automatically control at least some operations of the scanning system 100, for example. For example, the control system 126 may be configured to automatically and dynamically control the rate at which the support 108 moves through the examination region 110, the rate at which the rotor 106 rotates relative to the stator 104, activation, deactivation, and output level of (e.g., intensity of radiation emitted by) the radiation source(s) 114, or any combination or subcombination of these operating parameters. In some embodiments, the control system 126 may also accept manual override instructions from the terminal 122 and to issue instructions to the scanning system 100 to alter the operating parameters of the scanning system based on the manual override instructions.

Figure 2:
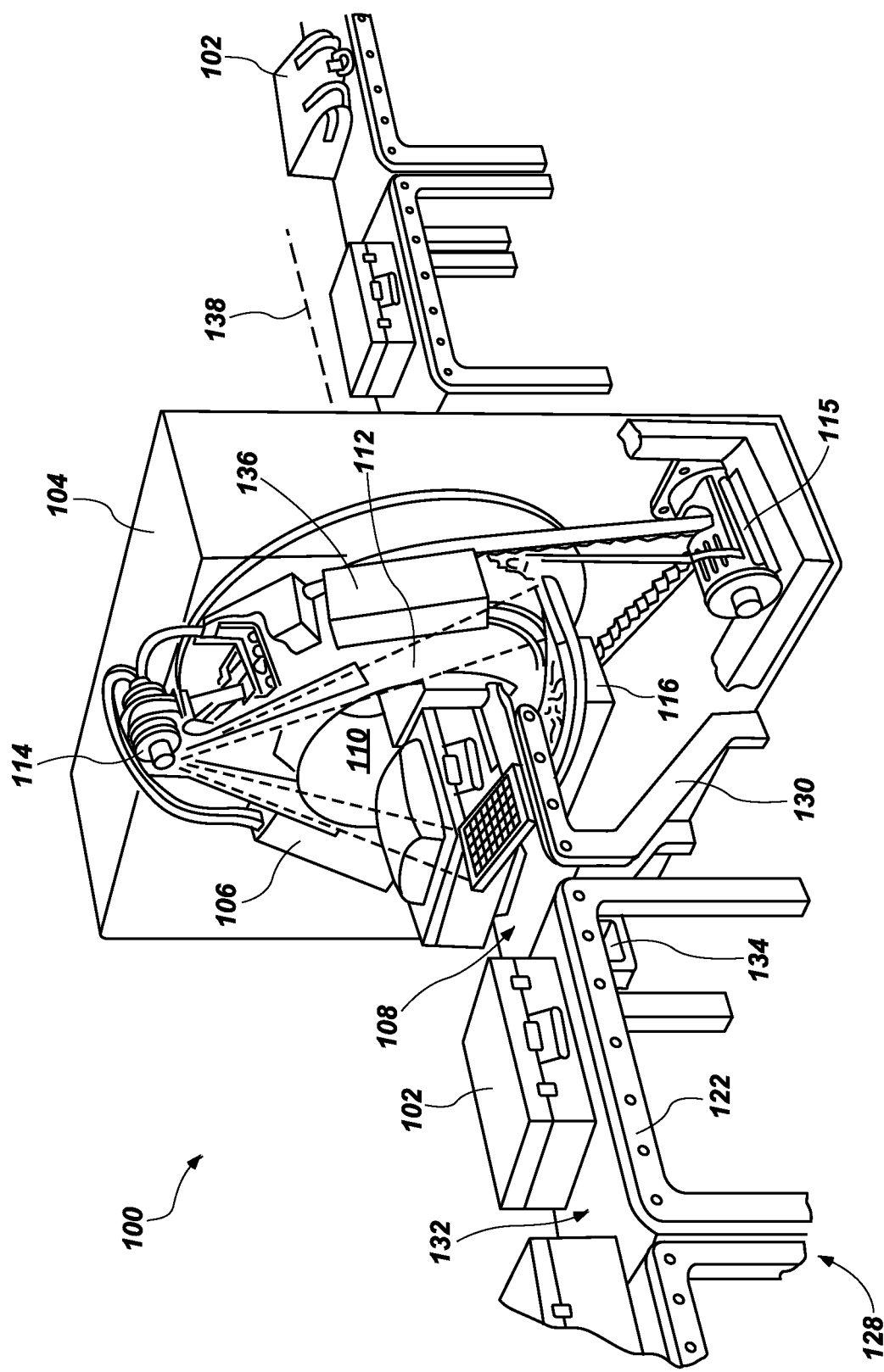
FIG. 2 is a perspective side view of a portion of the scanning system of FIG. 1.
Figure 3:
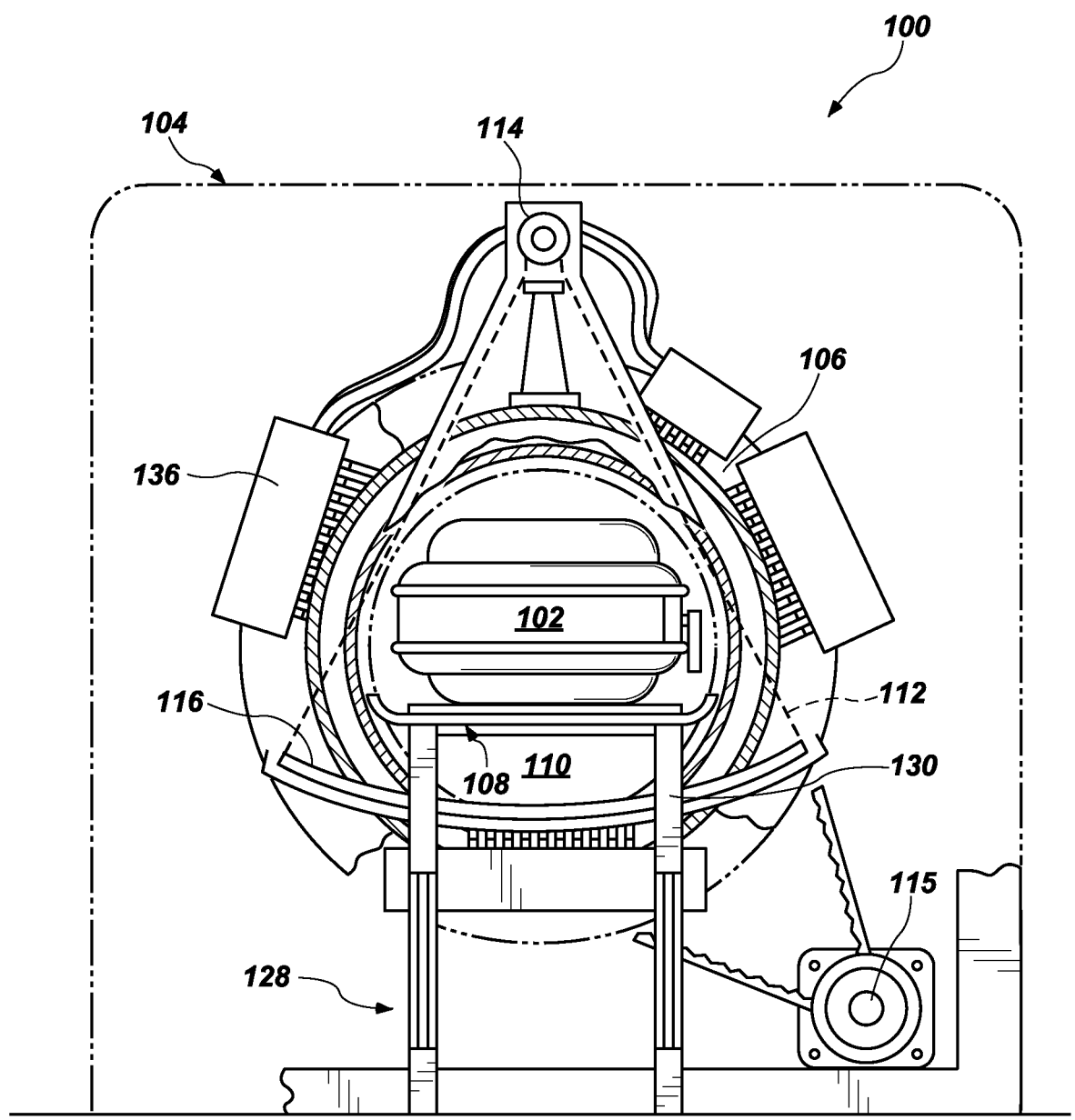
FIG. 3 is a front view of the portion of the scanning system of FIG. 2.

FIG. 2 is a perspective side view and FIG. 3 is a front view of a portion of the scanning system 100 of FIG. 1. Referring collectively to FIGS. 2 and 3, the scanning system 100 may be specifically configured as a baggage scanning system including an explosive detection system. The support 108 of the illustrated scanning system 100 may be configured as a conveyor system 128 configured to move objects 102 in the form of baggage, luggage, or other passenger items through the examination region 110 of the scanning system 100 so that helical scans can be performed on the objects 102. The conveyor system 128 may include, for example, belts 132 driven by motors 134 for supporting and transporting the objects 102. The speed of the motors 134 may control the linear rate at which the belts 132 transport the objects 102 supported thereon may proceed through the examination region 110. The control system 126 may issue command signals transmitted to the motors 134 (e.g., via a wireless or wired connection) to vary the speed of the motors 134 and associated belts 132. The conveyor system 128 may include, for example, several individual respective conveyors 130 (e.g., one conveyor 130 extending through the examination region 110, another conveyor 130 configured to convey objects 102 toward the scanning system 100, and another conveyor 130 configured to convey objects 102 away from the scanning system 100); however, other forms of conveyor systems may be used. The different conveyors 130 may be operated at different speeds in accordance with instructions issued by the control system 126.

The scanning system 100 may include a rotator 115 (e.g., motor, drive shaft, chain, etc.) configured to drive rotation of the rotor 106, and the radiation source(s) 114 and radiation detector(s) 116 supported thereon, relative to the stator 104. The rotator 115 specifically shown in FIGS. 2 and 3 is configured as a motor with a belt or chain mechanically engaged with the rotor 106 to cause the rotor 106 to rotate in response to movement of the motor and belt/chain. The speed of the rotator 115 may control the rotational rate at which the rotor 106 moves the radiation source(s) 114 and radiation detector(s) 116 supported thereby. The control system 126 may issue command signals transmitted to the rotator 115 (e.g., via a wireless or wired connection) to vary the speed of the motors 134 and associated belts 132. The scanning system 100 may also include shields 136, which may include a radiation-blocking material (e.g., lead) for reducing the likelihood that radiation emitted by the radiation source(s) 114 may propagate beyond the rotor 106 and/or stator 104.

Figure 4:
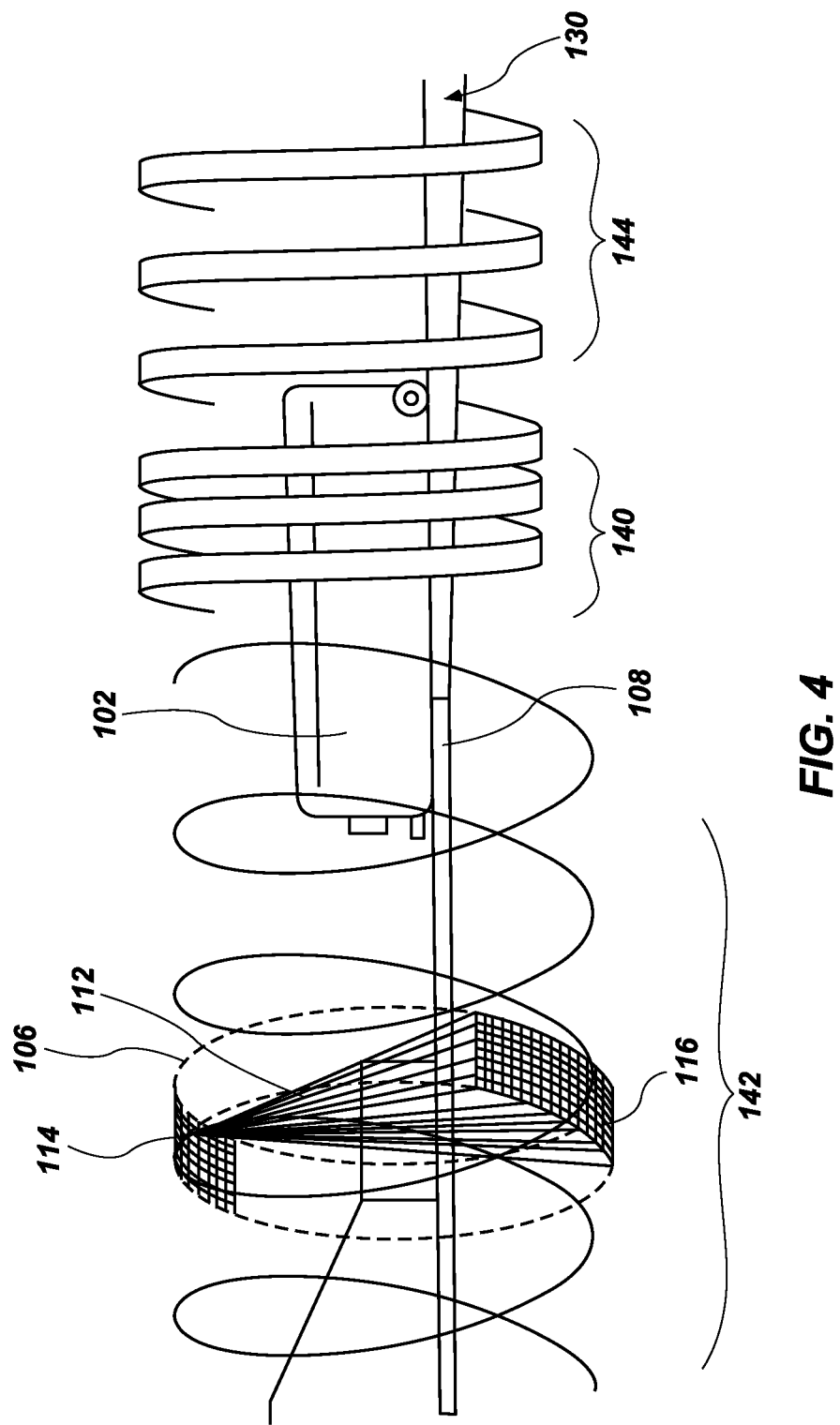
FIG. 4 is a graphical illustration of the concept of pitch in CT scanning.

FIG. 4 is a graphical illustration of the concept of pitch in CT scanning. To perform CT scanning, an object 102 for examination is translated in a direction parallel to an axis of rotation 138 of the rotor 106, utilizing the support 108 (e.g., a respective conveyor 130 of the conveyor system 128). The object 102 is exposed to radiation 112 while the object 102 is being translated linearly by the support 108. That is, one or more radiation sources 114 a emit radiation 112, causing the radiation to impact and extend into the object 102, attenuating the radiation 112. One or more radiation detectors 116 mounted on a substantially diametrically opposite side of the object 102 relative to the radiation source(s) 114 is configured to detect radiation 112 that has traversed the object 102.

When the scanning system 100 is in a finer pitch mode, the rotor 106 may complete more full rotations per unit of distance advanced by the object 102 (e.g., per effective width of the detector 116 at the axis of rotation 138), as illustrated in section 140. As a result, a greater number of cross-sections of the object 102 may be received at the radiation detector(s) 116, producing a higher-resolution image of the object 102 and its contents. When the scanning system 100 is in a coarser pitch mode, the rotor 106 may complete fewer full rotations per unit of distance advanced by the object 102 (e.g., per effective width of the detector 116 at the axis of rotation 138), as illustrated in section 142. As a result, the support 108 may operate at higher speeds, giving greater throughput, the rotor 106 may rotate at lower speeds, reducing wear and prolonging life, or both. When the scanning system 100 is in a medium pitch mode, the rotor 106 may complete a moderate amount of full rotations per unit of distance advanced by the object 102 (e.g., per effective width of the detector 116 at the axis of rotation 138), as illustrated in section 144. As a result, a moderate number of cross-sections of the object 102 may be received at the radiation detector(s) 116, the support 108 may operate at moderate speeds, and the rotor 106 may rotate at moderate speeds, achieving a balance between image resolution, throughput, and wear and useful life. As specific, nonlimiting examples, the rotor 106 may complete two or more full rotations per unit of distance advanced by the object 102 (e.g., per effective width of the detector 116 at the axis of rotation 138) when the scanning system 100 is in the finer pitch mode, the rotor 106 may complete one or fewer full rotations per unit of distance advanced by the object 102 (e.g., per effective width of the detector 116 at the axis of rotation 138) when the scanning system 100 is in the coarser pitch mode, and the rotor 106 may complete between 1.2 and 1.8 full rotations per unit of distance advanced by the object 102 (e.g., per effective width of the detector 116 at the axis of rotation 138) when the scanning system 100 is in the medium pitch mode.

The pitch may primarily be affected by the linear rate at which the support 108 transports the object 102 and the rotational rate at which the rotor 106 and its associated radiation source(s) 114 and radiation detector(s) 116 rotate about the object 102. As a result, the control system 126 (see FIG. 1) may alter the pitch of the scanning system 100 by changing the linear rate at which the support 108 transports the object 102, the rotational rate at which the rotor 106 and its associated radiation source(s) 114 and radiation detector(s) 116 rotate about the object 102, or both. In some embodiments, the pitch may be selectable (automatically and/or manually) from among several predefined pitches achieved utilizing preset operating parameters. In other embodiments, the pitch may be variable (at least substantially continuously or incrementally) from all potential pitches achievable (automatically and/or manually) utilizing whatever operational parameters (continuously variable or incremental) are selectable for the components of the rotator 115 (see FIGS. 1-3) and the motors 134 of the conveyor system (see FIGS. 2, 3).

Figure 5:
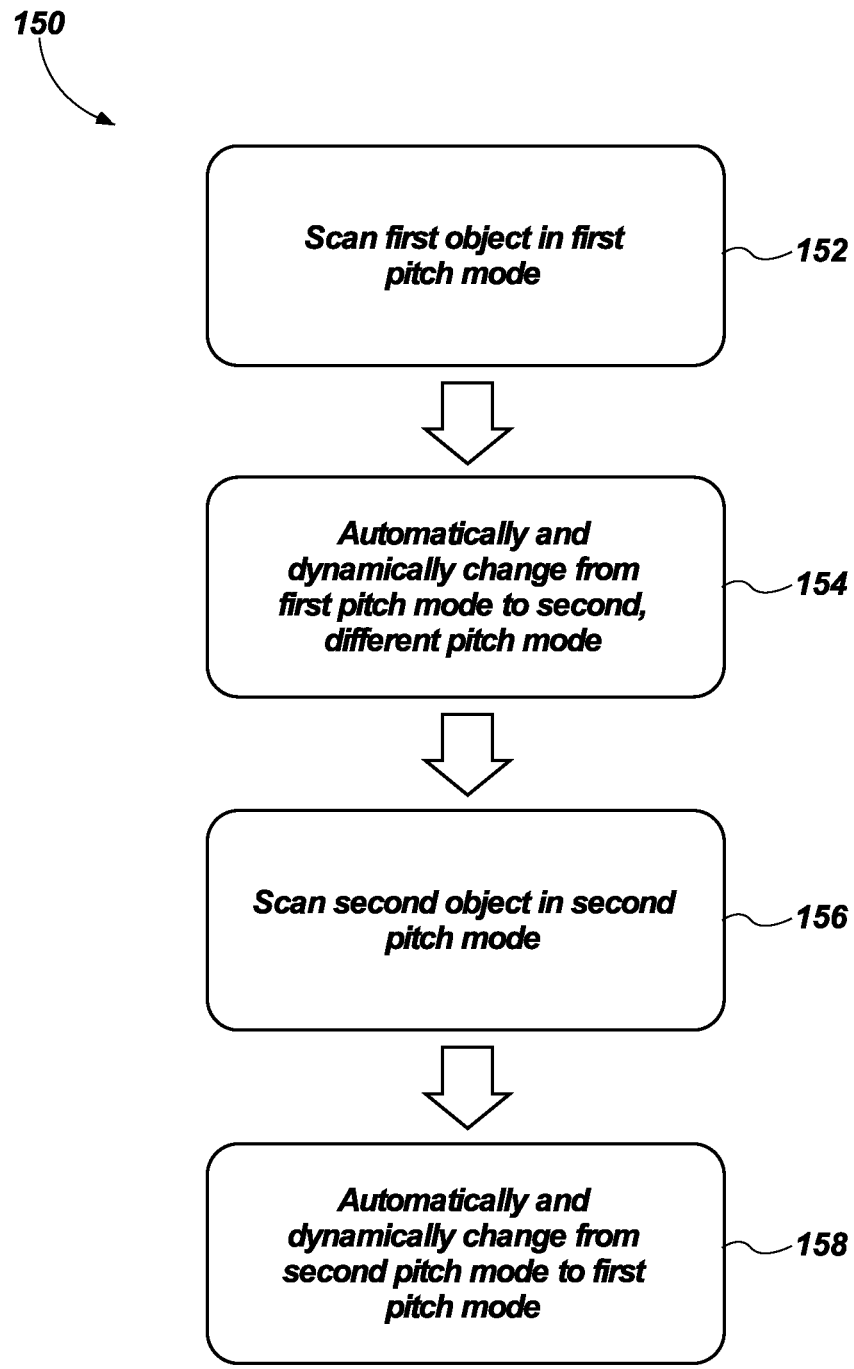
FIG. 5 is a flowchart of a method of operating the scanning system of FIG. 1.

FIG. 5 is a flowchart of a method 150 of operating the scanning system 100 of FIG. 1. The method 150 may involve scanning a first object 102 (see FIGS. 1-4) in a first pitch mode utilizing a scanning system 100 (see FIGS. 1-4), as indicated at act 152. This first pitch mode may correspond to, for example, a coarser pitch mode, in which a rate of rotation of the rotor 106 (see FIGS. 1-4) may be lower, a linear rate at which the conveyor system 128 moves the object 102 through the examination region 110 (see FIGS. 1-4) may be higher, or both. For example, to reduce system wear, the rotor 106 (see FIGS. 1-4) may rotate, for example, once per second and scan 1.8 times the effective width of the detector 116 (see FIGS. 1-4) at the axis of rotation 138 (see FIG. 2) (e.g., an isocenter) once per rotation of the rotor 106. To increase throughput, the rotor 106 (see FIGS. 1-4) may rotate, for example, at three and one-half rotations per second and scan up to 1.8 times the effective width of the detector 116 (see FIGS. 1-4) at the isocenter once per rotation of the rotor 106. As another example, the first pitch mode may correspond to a finer pitch mode, in which a rate of rotation of the rotor 106 (see FIGS. 1-4) may be higher, a linear rate at which the conveyor system 128 moves the object 102 through the examination region 110 (see FIGS. 1-4) may be lower, or both. In this case, the rotor 106 (see FIGS. 1-4) may rotate, for example, at twice per second and scan half the width of the detector 116 (see FIGS. 1-4) at the isocenter once per rotation of the rotor 106.

The method 150 may further involve automatically and dynamically changing from the first pitch mode to a second, different pitch mode, as indicated at act 154. In embodiments where the first pitch mode corresponds to a finer pitch mode, the second pitch mode may correspond to a coarser pitch mode. For example, the control system 126 may issue one or more control signals, causing the rate of rotation of the rotor 106 (see FIGS. 1-4) to decrease, the linear rate of advancement of the respective conveyor 130 passing through the examination region 110 (see FIGS. 1-4) to increase, or both when transitioning from the first pitch mode to the second pitch mode. In other embodiments where the first pitch mode corresponds to a coarser pitch mode, the second pitch mode may correspond to a finer pitch mode. For example, the control system 126 may issue one or more control signals, causing the rate of rotation of the rotor 106 (see FIGS. 1-4) to increase, the linear rate of advancement of the respective conveyor 130 passing through the examination region 110 (see FIGS. 1-4) to decrease, or both when transitioning from the first pitch mode to the second pitch mode.

The method 150 may then involve scanning a second object 102 (see FIGS. 1-4) in the second pitch mode utilizing the scanning system 100 (see FIGS. 1-4), as indicated at act 156. The method 150 may further involve automatically and dynamically changing from the second pitch mode back to the first pitch mode, as indicated at act 158. In embodiments where the second pitch mode corresponds to a finer pitch mode, the first pitch mode may correspond to a coarser pitch mode. For example, the control system 126 may issue one or more control signals, causing the rate of rotation of the rotor 106 (see FIGS. 1-4) to decrease, the linear rate of advancement of the respective conveyor 130 passing through the examination region 110 (see FIGS. 1-4) to increase, or both when transitioning from the second pitch mode to the first pitch mode. In other embodiments where the second pitch mode corresponds to a coarser pitch mode, the first pitch mode may correspond to a finer pitch mode. For example, the control system 126 may issue one or more control signals, causing the rate of rotation of the rotor 106 (see FIGS. 1-4) to increase, the linear rate of advancement of the respective conveyor 130 passing through the examination region 110 (see FIGS. 1-4) to decrease, or both when transitioning from the second pitch mode to the first pitch mode.

The first and second modes may correspond, for example, to predefined pitches produced from preselected operating parameters, and transitioning may involve stepping between the preselected operating parameters and resulting pitches. As another example, the first and second modes may be taken with reference to existing operational states, such that the exact pitches and associated operating parameters may not be drawn from preselected values and subsequent states for those modes may not necessarily match previous states, but changes from the present operational state may produce what may be referred to as a change in mode.

The changes in mode may be automatically effected in that the control system 126 may change the pitch without requiring input from an operator or other user 120 (see FIG. 1). For example, the control system 126 may be given access to information relevant to operation of the scanning system 100 utilizing a network connection (e.g., wired or wireless), or the scanning system 100 itself may generate feedback relevant to operation of the scanning system 100 that is accessible to the control system 126. The changes in mode may be dynamically effected in that the control system 126 may change the pitch in response to real-time updates, not just preset routines. As a result, the scanning system 100 may be improved by enabling the scanning system 100 to better adjust performance to ongoing prioritization of demands on performance without requiring human intervention. The control system 126 may further send information regarding the operational state of the scanning system 100 to the image generator 118, causing the image generator 118 to automatically and dynamically adjust the process of generating images from detected radiation 112 in real-time to produce images based on the change in scanning pitch.

Initial scanning is one example of a feedback characteristic that may cause the control system 126 to automatically and dynamically alter the pitch mode in which the scanning system 100 operates. For example, initial scanning performed by the radiation source(s) 114 and radiation detector(s) 116 of the scanning system itself (see FIGS. 1-4), or of another scanner positioned upstream of the scanning system (e.g., a line scanner positioned upstream from a CT scanner), may indicate that higher resolution image data for a scanned object is necessary to determine the scanned object's contents (e.g., because the object itself or its contents are particularly complex, shielded, or otherwise difficult to scan). As an example, if during initial screening an object 102 (see FIGS. 1-4) contains features less than twice the image pixel size, a rescan at a higher image resolution may be beneficial, and may be automatically conducted by adjusting the pitch of the scanning system 100. In such a situation, the control system 126 may automatically and dynamically cause the rotator 115 to rotate the rotor 106 at a faster rotational rate, the motor 134 of the respective conveyor 130 to advance the object 102 at a slower linear rate, or both. Optionally, the control system 126 may also or alternatively automatically cause a conveyor system to recirculate the object 102 to the same scanning system 100 or to another scanning system 100 (as indicated by recirculation process 161 in FIG. 6), or cause the monitor 124 to display a message instructing operators to recirculate the object 102 through the same scanning system 100 or another scanning system 100. As another example, initial scanning performed by the radiation source(s) 114 and radiation detector(s) 116 of the scanning system itself (see FIGS. 1-4), or of another scanner positioned upstream of the scanning system (e.g., a line scanner or another CT scanner positioned upstream from a subsequent CT scanner), may indicate that lower resolution image data for a scanned object is acceptable to determine the scanned object's contents (e.g., because the object itself or its contents are particularly simple, transparent to radiation, or otherwise easily scanned). In such a situation, the control system 126 may automatically and dynamically cause the rotator 115 to rotate the rotor 106 at a slower rotational rate, the motor 134 of the respective conveyor 130 to advance the object 102 at a faster linear rate, or both.

Airport schedule, place of origin, and place(s) of destination (e.g., final and/or any intermediate) are additional examples of a feedback characteristic that may cause the control system 126 to automatically and dynamically alter the pitch mode in which the scanning system 100 operates. For example, expected throughput at a security checkpoint based on flight schedules may indicate that additional scanning time is available without falling below a minimum throughput threshold (e.g., because the airport is operating significantly below peak potential traffic), place of origin and/or destination may indicate that dangerous and/or contraband items are more likely to be encountered, or a higher level of threat detection may otherwise be desirable. More specifically, expected throughput at a security checkpoint based on flight schedules may be about 20% or more below peak potential traffic (e.g., between about 25% and about 99% below peak recommended throughput). In such situations, the control system 126 may automatically and dynamically cause the rotator 115 to rotate the rotor 106 at a faster rotational rate, the motor 134 of the respective conveyor 130 to advance the object 102 at a slower linear rate, or both. As another example, expected throughput at a security checkpoint based on flight schedules may indicate that screening time must be decreased to avoid falling below a minimum throughput threshold (e.g., because the airport is operating at or above peak potential traffic), or place of origin and/or destination may indicate that dangerous and/or contraband items are less likely to be encountered. In such a situation, the control system 126 may automatically and dynamically cause the rotator 115 to rotate the rotor 106 at a slower rotational rate, the motor 134 of the respective conveyor 130 to advance the object 102 at a faster linear rate, or both.

Wear thresholds and use rates are additional examples of a feedback characteristic that may cause the control system 126 to automatically and dynamically alter the pitch mode in which the scanning system 100 operates. For example, a wear threshold for a given unit of time (e.g., hours operating at maximum operating speeds) may not yet have been reached for the rotator 115, the motor 134, or both. More specifically, the rotator 115 may have been operated at maximum operating speeds for 8 hours or more in a given 24-hour period. In such a situation, the control system 126 may automatically and dynamically cause the rotator 115 to rotate the rotor 106 at a slower rotational rate, the motor 134 of the respective conveyor 130 to advance the object 102 at a slower linear rate, or both. As another example, the wear threshold for a given unit of time (e.g., hours operating at or above recommended operating speeds) may have been reached or exceeded for the rotator 115, the motor 134, or both. In such a situation, the control system 126 may automatically and dynamically cause the rotator 115 to rotate the rotor 106 at a slower rotational rate, the motor 134 of the respective conveyor 130 to advance the object 102 at a slower linear rate, or both. In some embodiments, the control system 126 may prioritize the useful life of the rotor 106 and associated components of the useful life of the respective conveyor 130 and associated components, causing the rotor 106 to decrease or maintain speed while the respective conveyor 130 maintains or increases speed to achieve desired pitch.

Figure 6:
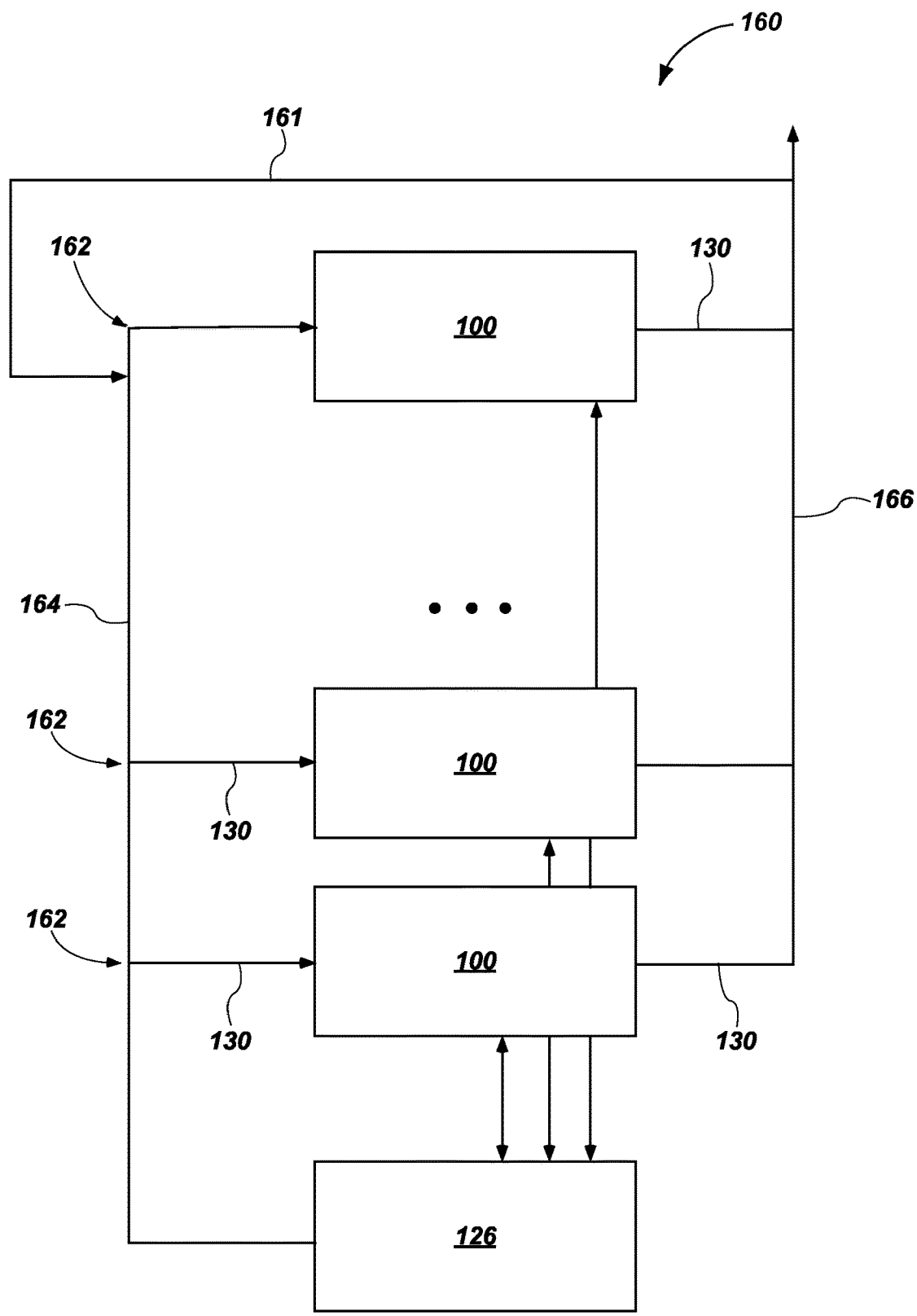
FIG. 6 is a schematic of an assembly of scanning systems.

FIG. 6 is a schematic of an assembly 160 of scanning systems 100. The assembly 160 may generally be configured to assign individual scanning systems 100 to respective groups operating in certain pitch modes. For example, the assembly 160 may assign a number of the scanning systems 100 to operate in a first pitch mode (as described previously in connection with FIG. 4) and another number of scanning systems 100 (e.g., a smaller, equal, or larger number) to operate in a second, different pitch mode (as described previously in connection with FIG. 4). Feedback characteristics causing individual scanning systems 100 to be assigned to a first group operating in the first pitch mode, a second group operating in the second pitch mode, reassigned from the first group to the second group, or reassigned from the second group to the first group may include, for example, airport schedule, place of origin, place(s) of destination, and/or wear thresholds and use rates, as described previously in connection with FIG. 5.

The assembly 160 may also generally be configured to route objects 102 to be scanned to those individual scanning systems 100 currently operating in pitch modes likely to provide appropriate scanning to the respective objects 102. For example, the conveyor system 128 may include a series of diverters 162, each diverter 162 configured to route incoming objects 102 from an input conveyor 164 of the conveyor system 128 toward respective conveyors 130 extending through examination regions 110 of individual scanning systems 100. The respective conveyors 130 may then be configured to convey objects 102 to a shared output conveyor 166 for outputting the scanned objects 102 from the assembly 160. One or more recirculation loops 161 may be incorporated to enable rescanning objects 102. The control system 126 may cause a given diverter to activate, routing an object 102 to a selected one of the scanning systems 100, based on, for example, those feedback characteristics discussed previously in connection with FIG. 5. For example, the control system 126 may route an object 102, or a greater proportion of objects 102, to a scanning system 100 operating in a finer pitch mode when expected throughput at a security checkpoint based on flight schedules may indicate that additional scanning time is available without falling below a minimum throughput threshold (e.g., because the airport is operating significantly below peak potential traffic), place of origin and/or destination may indicate that dangerous and/or contraband items are more likely to be encountered (e.g., because those places are in countries listed as state sponsors of terrorism), and/or a wear threshold for a given unit of time (e.g., hours operating at or above recommended operating speeds) may not yet have been reached for the rotator 115, the motor 134 (see FIGS. 2, 3), or both. As another example, the control system 126 may route an object 102, or a greater proportion of objects 102, to a scanning system 100 operating in a coarser pitch mode when expected throughput at a security checkpoint based on flight schedules may indicate that screening time must be decreased to avoid falling below a minimum throughput threshold (e.g., because the airport is operating at or above peak potential traffic), place of origin and/or destination may indicate that dangerous and/or contraband items are less likely to be encountered (e.g., because those places are in countries on a travel whitelist), and/or a wear threshold for a given unit of time (e.g., hours operating at or above recommended operating speeds) may have been reached for the rotator 115, the motor 134 (see FIGS. 2, 3), or both.

The control system 126 may also cause a given diverter 162 to activate, routing an object 102 to a selected one of the scanning systems 100, based on, for example, additional feedback characteristics relating to the objects 102 themselves or their known owners, such as, for example, to increase scan quality of the object(s) 102 or to increase throughput. For example, the control system 126 may route an object 102, or a greater proportion of objects 102, to a scanning system 100 operating in a finer pitch mode when place of origin and/or destination for the object(s) 102 may indicate that dangerous and/or contraband items are more likely to be encountered (e.g., because those places are in countries listed as state sponsors of terrorism), and/or owner identity may indicate that dangerous and/or contraband items are more likely to be encountered (e.g., because the owner is on a watch list for terrorism or has a known criminal record). As another example, the control system 126 may route an object 102, or a greater proportion of objects 102, to a scanning system 100 operating in a coarser pitch mode when place of origin and/or destination for the object(s) 102 may indicate that dangerous and/or contraband items are less likely to be encountered (e.g., because those places are in countries on a travel whitelist), and/or owner identity may indicate that dangerous and/or contraband items are less likely to be encountered (e.g., because the owner is on a white list).

Figure 7:
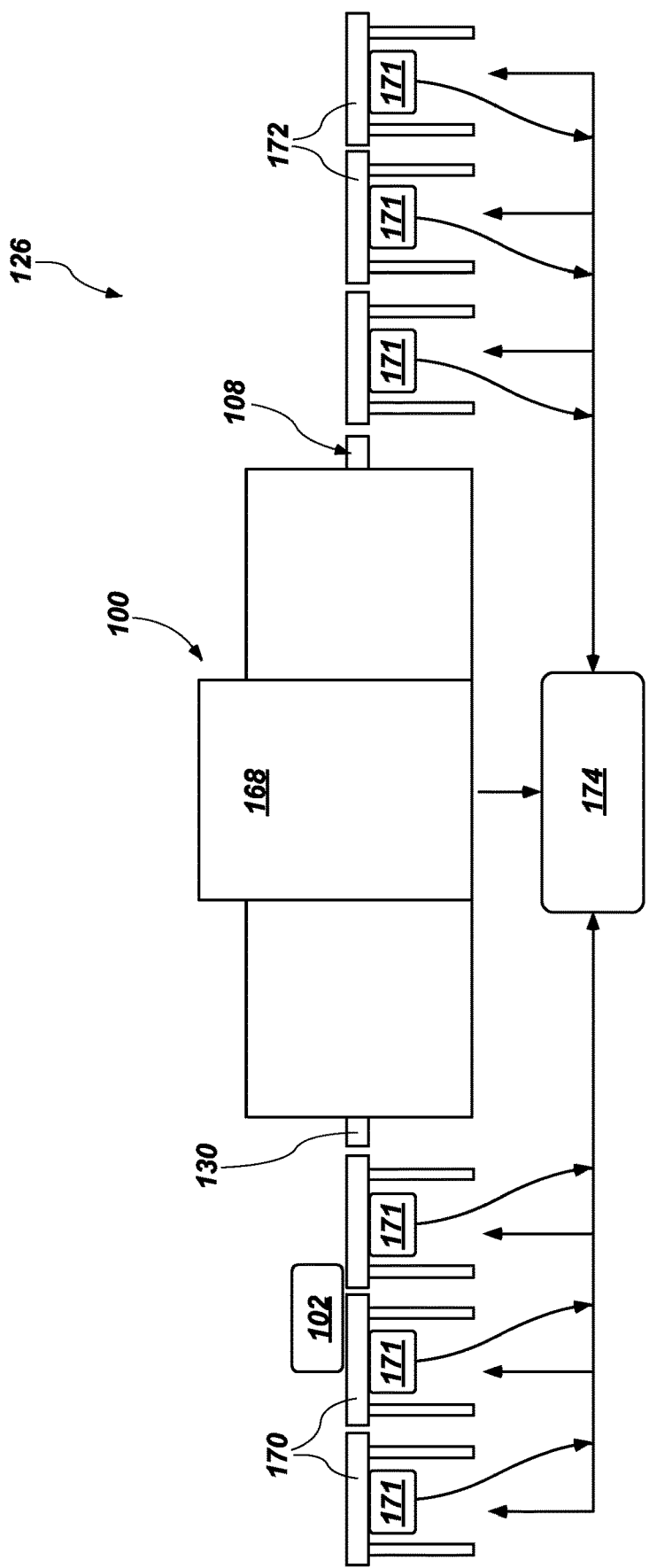
FIG. 7 is a schematic of one of the scanning systems of FIG. 6.

FIG. 7 is a schematic of one of the scanning systems 100 of FIG. 6. The scanning system 100 may include, for example, a housing 168, which may at least partially act as the stator 104, the shields 136 (see FIGS. 1-3), or both in some embodiments. The housing 168 may enclose, for example, a stator 104 in embodiments where the housing 168 itself does not act as the stator 104, a rotor 106, an examination region 110, a radiation source 114, a radiation detector 116, a portion of a support 108 in the form of a portion of the respective conveyor 130 extending through the examination region 110 in embodiments where the support 108 is a component of a conveyor system 128, and shields 136 in embodiments where the housing 168 itself does not act as the shields 136 (see FIGS. 1-3). In some embodiments, a control system 126 (see FIGS. 1-3), or a portion thereof, may be supported within or on the housing 168.

In embodiments where the support 108 is a component of a conveyor system 128, one or more respective input conveyors 170 may be configured to convey objects 102 from a diverter 162 at a shared input conveyor 164 (see FIG. 6) to the one or more respective input conveyors 170. The one or more respective input conveyors 170 may be configured to transport one or more object(s) 102 toward the respective conveyor 130, which may be configured to transport the object(s) 102 through the examination region 110 (see FIGS. 1-3). The respective conveyor 130 may be configured to convey objects 102 to one or more respective output conveyors 172, which may be configured to transport the object(s) 102 to a shared output conveyor 166 (see FIG. 6). Each respective input conveyor 170, each respective conveyor 130 extending through the examination region 110 (see FIGS. 1-3), and each respective output conveyor 172 may include its own motor 134 configured to control the rate at which a corresponding belt 132 linearly translates the object(s) 102 supported thereon through the scanning system 100. At least the input conveyors 170, and optionally the shared input conveyor 164 (see FIG. 6), the respective conveyors 130, the respective output conveyors 172, the shared output conveyor 166, or any combination or subcombination of these may be monitored utilizing one or more sensors 171 (e.g., photoeyes) operably coupled to at least the conveyor control module 174, and the sensors 171 and conveyor control module 174 may be cooperatively configured to determine the number, position, and optionally size of objects 102 supported thereon. At least the input conveyors 170, and optionally the shared input conveyor 164 (see FIG. 6), the respective conveyors 130, the respective output conveyors 172, the shared output conveyor 166, or any combination or subcombination of these may be operable at variable speeds, and may be configured to queue objects 102 for at least transmission to, and optionally passage through and/or transport away from, the housing 168.

In some embodiments, the control system 126 of the scanning system 100 may include a conveyor control module 174 configured to control operation of the conveyor system 128, including the input conveyor 164, diverters 162, one or more respective input conveyors 170, one or more respective conveyors 130 extending through corresponding individual examination regions 110, one or more respective output conveyors 172, and the output conveyor 166 (see also FIG. 6). The conveyor control module 174 may be configured to change the speeds of one or more motors 134, altering the rate at which a corresponding belt 132 linearly translates the object(s) 102 supported thereon and potentially modulating the scanning pitch of the scanning system 100, in response to detected or otherwise discernible characteristics of the object(s) 102, sensed operational parameters of the scanning system 100, and/or throughput information for the associated facility (e.g., an airport), as described previously in connection with FIGS. 1 through 6.

Figure 8:
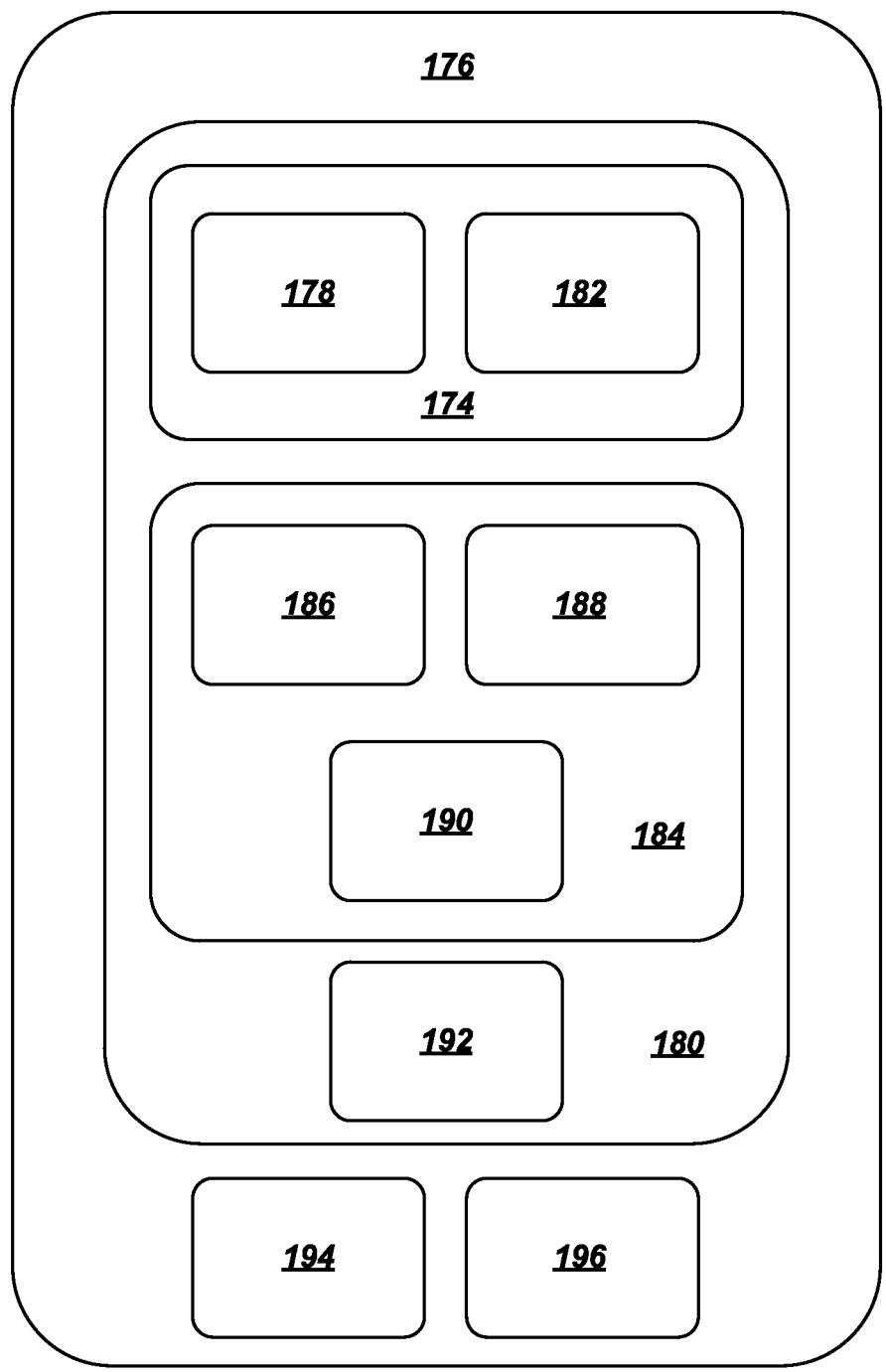
FIG. 8 is a schematic of a controller for the scanning system of FIG. 7.

FIG. 8 is a schematic of a controller 176 for the scanning system 100 of FIG. 7 or for the assembly 160 of scanning systems 100. The controller 176 may be incorporated in a control system 126 (see FIGS. 1-3). The controller 176 may include multiple functional modules, which may be deployed as separate physical devices or device components, or may be incorporated into a single physical device or component for a device with distinct modules deployed in software. For example, the controller 176 may include a pitch control module 180 configured to modulate the scanning pitch of one or more operatively connected scanning systems 100 (see FIGS. 1-3, 6, 7), as described previously in connection with FIGS. 1 through 7.

As another example, the pitch control module 180 of the controller 176 may include a conveyor control module 174 configured to control operation of the conveyor system 128. More specifically, the conveyor control module 174 may include, for example, a motor speed module 178 configured to determine and modulate the operating speed of each operatively connected motor 134 (e.g., utilizing data collected from sensors positioned to sense the operating speed of the respective motors 134). The conveyor control module 174 may further include, for example, a conveyor speed module 182 configured to determine the operating speed of the belt 132 of each operatively connected conveyor 128, 130, 164, 166, 170, 172 (see FIGS. 1-3, 6, 7) (e.g., utilizing data collected from sensors positioned to sense the operating speed of the respective belts 132) and indicate whether the operating speed of each associated motor 134 correlates with the expected output speed of the belt 132 of each operatively connected conveyor 128, 130, 164, 166, 170, 172 (see FIGS. 1-3, 6, 7).

As yet another example, the pitch control module 180 of the controller 176 may include a scanner control module 184 configured to control operation of the scanning components of the scanning system 100. More specifically, the scanner control module 184 may include, for example, a rotator speed module 186 configured to determine and modulate the operating speed of each operatively connected rotator 115 (e.g., utilizing data collected from sensor positioned to sense the operating speed of the respective rotators 115). The scanner control module 184 may further include, for example, a rotor speed module 188 configured to determine the operating speed of the rotor 106 of each operatively connected scanning system 100 (see FIGS. 1-3, 6, 7) (e.g., utilizing data collected from sensors positioned to sense the operating speed of the respective rotors 106) and indicate whether the operating speed of each associated rotor 106 correlates with the expected output speed from the rotator 115 (see FIGS. 1-3, 6, 7). The scanner control module 184 may further include, for example, a radiation intensity module 190 configured to determine the operational state and intensity of radiation 112 emitted by the radiation source(s) 114 of each operatively connected scanning system 100 (see FIGS. 1-3, 6, 7) (e.g., utilizing data collected from the radiation detector(s) 116).

As still further examples, the pitch control module 180 may include, for example, an object speed module 192 configured to determine the rate at which object(s) 102 advance linearly along the conveyor system 128 (see FIGS. 1-3, 6, 7) (e.g., utilizing data collected from sensors positioned to sense the movement of object(s) 102) and indicate whether the detected linear speed of each object 102 correlates with the expected output speed from each operatively connected conveyor 128, 130, 164, 166, 170, 172 (see FIGS. 1-3, 6, 7). The controller 176 may further include, for example, an image generation module 194 configured to adjust the way in which the image generator 118 utilizes data from the radiation detector(s) 116 to generate accurate depictions of scanned object(s) 102 and their contents based on real-time changes to the scanning pitch of the scanning system(s) 100. The controller 176 may also include, for example, a user input module 196 configured to accept user input from the terminal 122 and apply the user input to modulate operating parameters of the associated scanning system(s) 100 and/or conveyor system(s) 128 based on the user input and any safety protocols limiting the ways in which user input may affect the operating parameters of the associated scanning system(s) 100 and/or conveyor system(s) 128.

Specific implementations shown and described are only examples and should not be construed as the only way to implement the present disclosure unless specified otherwise herein. Elements, circuits, and functions may be shown in block diagram form in order not to obscure the present disclosure in unnecessary detail. Conversely, specific implementations shown and described are by way of example only and should not be construed as the only way to implement the present disclosure unless specified otherwise herein. Additionally, block definitions and partitioning of logic between various blocks is/are examples of a specific implementation. It will be readily apparent to one of ordinary skill in the art that the present disclosure may be practiced by numerous other partitioning solutions. For the most part, details concerning timing considerations and the like have been omitted where such details are not necessary to obtain a complete understanding of the present disclosure and are within the abilities of persons of ordinary skill in the relevant art.

Many of the functional units described in this specification may be illustrated, described or labeled as logic, modules, threads, or other segregations of programming code, in order to more particularly emphasize their implementation independence in accomplishing the features, functions, tasks or steps that are generally described herein. The various illustrative logical blocks, modules, and circuits described in connection with the embodiments disclosed herein may be at least partially implemented or performed with a general purpose processor, a special purpose processor, a Digital Signal Processor (DSP), an Application Specific Integrated Circuit (ASIC), a Field Programmable Gate Array (FPGA) or other programmable logic device, discrete gate or transistor logic, discrete hardware components, or any combination thereof designed to perform the functions described herein.

These logic and modules may also be implemented using software or firmware, stored on a computer readable storage medium that is not a transitory signal, in system memory, or a combination thereof for execution by various types of processors.

In the case of a computer, these logic and modules may be embodied in software classes and applications executed by processor cores, and while the modules are executing the computer may be thought of as special-purpose or specific-purpose. The logic and modules may also relate to specific purpose hardware, including the firmware and machine code, controlling its operation. An identified module of executable code may, for instance, comprise one or more physical or logical blocks of computer instructions, which may, for instance, be organized as a thread, object, procedure, or function. Nevertheless, the executable of an identified module need not be physically located together, but may comprise disparate instructions stored in different locations which, when joined logically together, comprise the module and achieve the stated purpose for the module.

A module of executable code may comprise a single instruction, or many instructions, and may even be distributed over several different code segments, among different programs, and across several storage or memory devices.

Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network. Where a module or portions of a module are implemented in software, the software portions are stored on one or more physical devices, which are referred to herein as computer readable media.

In some embodiments, the software portions are stored in a non-transitory state such that the software portions, or representations thereof, persist in the same physical location for a period of time. Additionally, in some embodiments, the software portions are stored on one or more storage mediums that are not transitory signals, which include hardware elements capable of storing non-transitory states and/or signals representative of the software portions, even though other portions of the non-transitory storage mediums may be capable of altering and/or transmitting the signals. Examples of such storage mediums are flash memory and random-access-memory (RAM). Another example of a storage medium includes a read-only memory (ROM) which can store signals and/or states representative of the software portions for a period of time. However, the ability to store the signals and/or states is not diminished by further functionality of transmitting signals that are the same as, or representative of, the stored signals and/or states. For example, a processor may access the ROM to obtain signals that are representative of the stored signals and/or states in order to execute the corresponding software instructions.

A processor (which may also be characterized herein as a host processor or simply a host) may be a microprocessor, but in the alternative, the processor may be any processor, controller, microcontroller, or state machine. A processor may also be implemented as a combination of computing devices, such as a combination of a DSP and a microprocessor, a plurality of microprocessors, one or more microprocessors in conjunction with a DSP core, or any other such configuration. A computer including a processor is considered a special-purpose computer when the computer is configured to execute computing instructions (e.g., software code) related to embodiments of the present disclosure.

The embodiments disclosed herein may be described in terms of a process that is depicted as a flowchart, a flow diagram, a structure diagram, or a block diagram. Although a flowchart may describe operational acts as a sequential process, many of these acts can be performed in another sequence, in parallel, or substantially concurrently. In addition, the order of the acts may be rearranged. A process may correspond to a method, a thread, a function, a procedure, a subroutine, a subprogram, etc. Furthermore, the methods disclosed herein may be implemented in hardware, software, or both. If implemented in software, the functions may be stored or transmitted as one or more instructions or code on computer-readable media. Computer-readable media includes both computer storage media and communication media including any medium that facilitates transfer of a computer program from one place to another.

Various embodiments described herein may include elements described as implemented in a "workstation," "terminal," "computer," or a "computer system." Here, the terms "workstation," "terminal," "computer," and "computer system" are to be understood to include at least one non-transitory computer readable medium and at least one processing unit. In general, the storage medium will store, at one time or another, at least portions of an executable program code, and the processor(s) will execute one or more of the instructions included in that executable program code. It will be appreciated that the term "executable program code" and the term "software" mean substantially the same thing for the purposes of this description. It is not necessary to the practice of the various embodiments described herein that the storage medium and the processing unit be physically located in the same place. That is to say, it is foreseen that the processor and the memory might be distributed among physical pieces of equipment or even in geographically distinct locations. One of ordinary skill in the art will appreciate that "media," "medium," "storage medium," "computer-readable media," or "computer readable medium" as used here, may include a diskette, a magnetic tape, a digital tape, a compact disc, an integrated circuit, a ROM, a CD, DVD, Blu-Ray, a cartridge, flash memory, PROM, a RAM, a memory stick or card, or any other non-destructive storage medium useable by computers, including those that are re-writable.

Although the enabling software might be "written on" a disc, "embodied in" an integrated circuit, "carried over" a communications circuit, "stored in" a memory chip, or "loaded in" a cache memory, it will be appreciated that, for the purposes of this disclosure, the software will be referred to simply as being "in" or "on" a main memory that is a computer readable medium. Thus, the terms "in" or "on" are intended to encompass the above mentioned and all equivalent and possible ways in which software can be associated with a computer readable medium.

Users may interact with the computer systems described herein by way of graphical user interfaces (GUI) on a display and input devices such as touchscreens, keyboards, a computer mouse, touchpads, buttons, switches, jumpers, and the like. A GUI may include a console and/or dashboard and a user may interact with the GUI and, in-turn, underlying software applications.

Those of ordinary skill in the art would understand that information and signals may be represented using any of a variety of different technologies and techniques. For example, data, instructions, commands, information, signals, bits, symbols, and chips that may be referenced throughout this description may be represented by voltages, currents, electromagnetic waves, magnetic fields or particles, optical fields or particles, or any combination thereof. Some drawings may illustrate signals as a single signal for clarity of presentation and description. It will be understood by a person of ordinary skill in the art that the signal may represent a bus of signals, wherein the bus may have a variety of bit widths and the present disclosure may be implemented on any number of data signals including a single data signal.

Systems, assemblies, and methods for scanning objects in accordance with this disclosure may represent an improvement because they may increase the useful life of the scanners (or at least the most expensive components thereof), may better match the scanning performed to the needs of the associated airport, objects, and travelers, and may more seamlessly adjust performance in response to real-time changes to those needs.

Additional, nonlimiting embodiments within the scope of this disclosure include the following:

Embodiment 1: A scanning system, comprising: at least one scanning system configured to perform computed tomography scanning, each scanning system comprising a stator, a rotor supporting at least one radiation source and at least one radiation detector rotatable with the rotor, and a rotator operatively connected to the rotor to rotate the rotor relative to the stator; a conveyor system comprising a respective conveyor extending through the rotor of each scanning system; and a control system operatively connected to the scanning system and the conveyor system, the control system configured to automatically and dynamically increase a rate at which the rotor moves, decrease a rate at which the respective conveyor moves, or both when the control system enters a finer pitch mode and to automatically and dynamically decrease a rate at which the rotor moves, increase a rate at which the respective conveyor moves, or both when the control system enters a coarser pitch mode.

Embodiment 2: The scanning system of Embodiment 1, wherein the control system is configured to automatically and dynamically enter the finer pitch mode in response to initial scanning determining that higher resolution image data for a scanned object is necessary to determine the scanned object's contents.

Embodiment 3: The scanning system of Embodiment 1 or Embodiment 2, wherein the control system is configured to enter the finer pitch mode in response to expected passenger throughput, flight origin, or flight destination indicating that additional screening time is available without falling below a minimum throughput threshold or dangerous items are more likely to be encountered.

Embodiment 4: The scanning system of any one of Embodiments 1 through 3, wherein the control system is configured to enter the finer pitch mode in response to the control system determining that a wear threshold for a given unit of time has been reached for the scanning system, the conveyor system, or both.

Embodiment 5: The scanning system of any one of Embodiments 1 through 4, wherein the control system is configured to enter the coarser pitch mode in response to initial scanning determining that lower resolution image data for a scanned object is acceptable to determine the scanned object's contents.

Embodiment 6: The scanning system of any one of Embodiments 1 through 5, wherein the control system is configured to enter the coarser pitch mode in response to expected passenger throughput, flight origin, or flight destination indicating that screening time must be decreased to avoid falling below a minimum throughput threshold or dangerous items are less likely to be encountered.

Embodiment 7: The scanning system of any one of Embodiments 1 through 6, wherein the control system is configured to enter the coarser pitch mode in response to the control system determining that a wear threshold for a given unit of time has not yet been reached for the scanning system and the conveyor system.

Embodiment 8: An assembly of scanning systems, comprising: a first group of scanning systems configured to perform computed tomography scanning at a first pitch and a second group of scanning systems configured to perform computed tomography scanning at a second, finer pitch, each of the first group of scanning systems and the second group of scanning systems comprising at least one scanning system, each scanning system comprising a stator, a rotor supporting at least one radiation source and at least one radiation detector rotatable with the rotor, and a rotator operatively connected to the rotor to rotate the rotor relative to the stator; a conveyor system comprising an input conveyor, a respective conveyor operatively connected of the input conveyor and extending through the rotor of each scanning system, and an output conveyor operatively connected to each respective conveyor; and a control system operatively connected to the scanning system and the conveyor system, the control system configured to automatically and dynamically assign at least one scanning system from the first group of scanning systems to the second group of scanning systems, causing the at least one scanning system to increase a rate at which the rotor moves, decrease a rate at which the respective conveyor moves, or both to increase average scan quality, and to automatically and dynamically assign at least another scanning system from the second group of scanning systems to the first group of scanning systems, causing the at least another scanning system to decrease a rate at which the rotor moves, increase a rate at which the respective conveyor moves, or both to increase throughput.

Embodiment 9: The assembly of Embodiment 8, wherein the conveyor system comprises a diverter, and the control system is configured to cause the diverter to send an object to the first group of scanning systems to increase scan quality of the object or to send the object to the second group of scanning systems to increase throughput.

Embodiment 10: The assembly of Embodiment 9, wherein the control system is configured to cause the diverter to send the object to the first group of scanning systems in response to place of origin, final destination, or owner identity indicating that dangerous items are less likely to be encountered.

Embodiment 11: The assembly of Embodiment 9 or Embodiment 10, wherein the control system is configured to cause the diverter to send the object to the second group of scanning systems in response to place of origin, final destination, or owner identity indicating that dangerous items are more likely to be encountered.

Embodiment 12: The assembly of any one of Embodiments 8 through 11, wherein the control system is configured to automatically and dynamically assign the at least one scanning system from the first group of scanning systems to the second group of scanning systems, causing the at least one scanning system to increase a rate at which the rotor moves, decrease a rate at which the respective conveyor moves, or both in response to expected passenger throughput, flight origin, or flight destination indicating that additional screening time is available without falling below a minimum throughput threshold or dangerous items are more likely to be encountered.

Embodiment 13: The assembly of any one of Embodiments 8 through 12, wherein the control system is configured to automatically and dynamically assign the at least one scanning system from the first group of scanning systems to the second group of scanning systems, causing the at least one scanning system to increase a rate at which the rotor moves, decrease a rate at which the respective conveyor moves, or both in response to the control system determining that a wear threshold for a given unit of time has been reached for the scanning system, the conveyor system, or both.

Embodiment 14: The assembly of any one of Embodiments 8 through 13, wherein the control system is configured to automatically and dynamically assign at least another scanning system from the second group of scanning systems to the first group of scanning systems, causing the at least another scanning system to decrease a rate at which the rotor moves, increase a rate at which the respective conveyor moves, or both in response to expected passenger throughput, flight origin, or flight destination indicating that screening time must be decreased to avoid falling below a minimum throughput threshold or dangerous items are less likely to be encountered.

Embodiment 15: The assembly of any one of Embodiments 8 through 14, wherein the control system is configured to automatically and dynamically assign at least another scanning system from the second group of scanning systems to the first group of scanning systems, causing the at least another scanning system to decrease a rate at which the rotor moves, increase a rate at which the respective conveyor moves, or both in response to the control system determining that a wear threshold for a given unit of time has not yet been reached for the scanning system and the conveyor system.

Embodiment 16: A method of operating a scanning system, comprising: scanning a first object in a first, finer pitch mode utilizing a scanning system configured to perform computed tomography scanning by rotating a rotor supporting at least one radiation source and at least one radiation detector rotatable with the rotor relative to a stator at a first rotational rate utilizing a rotator operatively connected to the rotor and causing a conveyor extending through the rotor of the scanning system to move the first object past the at least one radiation source and the at least one radiation detector at a first linear rate; causing the scanning system to switch from the first, finer pitch mode to a second, coarser pitch mode utilizing a control system operatively connected to the scanning system and the conveyor by rotating the rotor at a second, slower rotational rate utilizing the rotator, causing the conveyor to move at a second, faster linear rate, or both; and scanning a second, different object in the second, coarser pitch mode by rotating the rotor at the second, slower rotational rate utilizing the rotator, causing the conveyor to move the second object past the at least one radiation source and the at least one radiation detector at the second, faster linear rate, or both.

Embodiment 17: The method of Embodiment 16, wherein the scanning system is one of many scanning systems in an assembly of the scanning systems and further comprising automatically and dynamically assigning the scanning system from a first group of scanning systems operating in the first, finer pitch mode to a second group of scanning systems operating in the second, coarser pitch mode to increase average scan quality, and to automatically and dynamically assign the scanning system from the second group of scanning systems to the first group of scanning systems to increase throughput.

Embodiment 18: The assembly of Embodiment 17, wherein the conveyor is one of many conveyors in a conveyor system comprising a diverter and further comprising causing the diverter to send another object to the first group of scanning systems to increase scan quality or to send the other object to the second group of scanning systems to increase throughput.

Embodiment 19: The assembly of Embodiment 18, further comprising causing the diverter to send the object to the second group of scanning systems in response to place of origin, final destination, or owner identity indicating that dangerous items are more likely to be encountered.

Embodiment 20: The scanning system of any one of Embodiments 16 through 19, further comprising automatically and dynamically placing the scanning system in the first, finer pitch mode in response to initial scanning determining that higher resolution image data for a scanned object is necessary to determine the scanned object's contents.

Embodiment 21: Computer-readable media including computer-executable instructions, which when executed cause a control system for a scanning system to: scan a first object in a first, finer pitch mode utilizing a scanning system configured to perform computed tomography scanning by rotating a rotor supporting at least one radiation source and at least one radiation detector rotatable with the rotor relative to a stator at a first rotational rate utilizing a rotator operatively connected to the rotor and causing a conveyor extending through the rotor of the scanning system to move the first object past the at least one radiation source and the at least one radiation detector at a first linear rate; cause the scanning system to switch from the first, finer pitch mode to a second, coarser pitch mode by rotating the rotor at a second, slower rotational rate utilizing the rotator, causing the conveyor to move at a second, faster linear rate, or both; and scan a second, different object in the second, coarser pitch mode by rotating the rotor at the second, slower rotational rate utilizing the rotator, causing the conveyor to move the second object past the at least one radiation source and the at least one radiation detector at the second, faster linear rate, or both.

While certain illustrative embodiments have been described in connection with the figures, those of ordinary skill in the art will recognize and appreciate that the scope of this disclosure is not limited to those embodiments explicitly shown and described in this disclosure. Rather, many additions, deletions, and modifications to the embodiments described in this disclosure may be made to produce embodiments within the scope of this disclosure, such as those specifically claimed, including legal equivalents. In addition, features from one disclosed embodiment may be combined with features of another disclosed embodiment while still being within the scope of this disclosure, as contemplated by the inventor.

What is claimed is:

1. A scanning system, comprising:
   at least one scanning system configured to perform computed tomography scanning, each scanning system comprising a stator, a rotor supporting at least one radiation source and at least one radiation detector rotatable with the rotor, and a rotator operatively connected to the rotor to rotate the rotor relative to the stator;
   a conveyor system comprising a respective conveyor extending through the rotor of each scanning system; and
   a control system operatively connected to the scanning system and the conveyor system, the control system configured to automatically and dynamically increase a rate at which the rotor moves, decrease a rate at which the respective conveyor moves, or both when the control system enters a finer pitch mode and to automatically and dynamically decrease a rate at which the rotor moves, increase a rate at which the respective conveyor moves, or both when the control system enters a coarser pitch mode;
   wherein the control system is configured to automatically and dynamically enter the finer pitch mode in response to initial scanning determining that higher resolution image data for a scanned object is necessary to determine the scanned object's contents.

2. The scanning system of claim 1, wherein the control system is configured to enter the finer pitch mode in response to expected passenger throughput, flight origin, or flight destination indicating that additional screening time is available without falling below a minimum throughput threshold or dangerous items are more likely to be encountered.

3. The scanning system of claim 1, wherein the control system is configured to enter the finer pitch mode in response to the control system determining that a wear threshold for a given unit of time has been reached for the scanning system, the conveyor system, or both.

4. The scanning system of claim 1, wherein the control system is configured to enter the coarser pitch mode in response to initial scanning determining that lower resolution image data for a scanned object is acceptable to determine the scanned object's contents.

5. The scanning system of claim 1, wherein the control system is configured to enter the coarser pitch mode in response to expected passenger throughput, flight origin, or flight destination indicating that screening time must be decreased to avoid falling below a minimum throughput threshold or dangerous items are less likely to be encountered.

6. The scanning system of claim 1, wherein the control system is configured to enter the coarser pitch mode in response to the control system determining that a wear threshold for a given unit of time has not yet been reached for the scanning system and the conveyor system.

7. An assembly of scanning systems, comprising:
a first group of scanning systems configured to perform computed tomography scanning at a first pitch and a second group of scanning systems configured to perform computed tomography scanning at a second, finer pitch, each of the first group of scanning systems and the second group of scanning systems comprising at least one scanning system, each scanning system comprising a stator, a rotor supporting at least one radiation source and at least one radiation detector rotatable with the rotor, and a rotator operatively connected to the rotor to rotate the rotor relative to the stator;
a conveyor system comprising an input conveyor, a respective conveyor operatively connected of the input conveyor and extending through the rotor of each scanning system, and an output conveyor operatively connected to each respective conveyor; and
a control system operatively connected to the scanning system and the conveyor system, the control system configured to automatically and dynamically assign at least one scanning system from the first group of scanning systems to the second group of scanning systems, causing the at least one scanning system to increase a rate at which the rotor moves, decrease a rate at which the respective conveyor moves, or both to increase average scan quality, and to automatically and dynamically assign at least another scanning system from the second group of scanning systems to the first group of scanning systems, causing the at least another scanning system to decrease a rate at which the rotor moves, increase a rate at which the respective conveyor moves, or both to increase throughput;
wherein the control system is configured to automatically and dynamically assign the at least one scanning system from the first group of scanning systems to the second group of scanning systems in response to initial scanning determining that higher resolution image data for a scanned object is necessary to determine the scanned object's contents.

8. The assembly of claim 7, wherein the conveyor system comprises a diverter, and the control system is configured to cause the diverter to send an object to the first group of scanning systems to increase scan quality of the object or to send the object to the second group of scanning systems to increase throughput.

9. The assembly of claim 8, wherein the control system is configured to cause the diverter to send the object to the first group of scanning systems in response to place of origin, final destination, or owner identity indicating that dangerous items are less likely to be encountered.

10. The assembly of claim 8, wherein the control system is configured to cause the diverter to send the object to the second group of scanning systems in response to place of origin, final destination, or owner identity indicating that dangerous items are more likely to be encountered.

11. The assembly of claim 7, wherein the control system is configured to automatically and dynamically assign the at least one scanning system from the first group of scanning systems to the second group of scanning systems, causing the at least one scanning system to increase a rate at which the rotor moves, decrease a rate at which the respective conveyor moves, or both in response to expected passenger throughput, flight origin, or flight destination indicating that additional screening time is available without falling below a minimum throughput threshold or dangerous items are more likely to be encountered.

12. The assembly of claim 7, wherein the control system is configured to automatically and dynamically assign the at least one scanning system from the first group of scanning systems to the second group of scanning systems, causing the at least one scanning system to increase a rate at which the rotor moves, decrease a rate at which the respective conveyor moves, or both in response to the control system determining that a wear threshold for a given unit of time has been reached for the scanning system, the conveyor system, or both.

13. The assembly of claim 7, wherein the control system is configured to automatically and dynamically assign at least another scanning system from the second group of scanning systems to the first group of scanning systems, causing the at least another scanning system to decrease a rate at which the rotor moves, increase a rate at which the respective conveyor moves, or both in response to expected passenger throughput, flight origin, or flight destination indicating that screening time must be decreased to avoid falling below a minimum throughput threshold or dangerous items are less likely to be encountered.

14. The assembly of claim 7, wherein the control system is configured to automatically and dynamically assign at least another scanning system from the second group of scanning systems to the first group of scanning systems, causing the at least another scanning system to decrease a rate at which the rotor moves, increase a rate at which the respective conveyor moves, or both in response to the control system determining that a wear threshold for a given unit of time has not yet been reached for the scanning system and the conveyor system.

15. A method of operating a scanning system, comprising:
scanning a first object in a first, finer pitch mode utilizing a scanning system configured to perform computed tomography scanning by rotating a rotor supporting at least one radiation source and at least one radiation detector rotatable with the rotor relative to a stator at a first rotational rate utilizing a rotator operatively connected to the rotor and causing a conveyor extending through the rotor of the scanning system to move the first object past the at least one radiation source and the at least one radiation detector at a first linear rate;
automatically and dynamically causing the scanning system to switch from the first, finer pitch mode to a second, coarser pitch mode utilizing a control system operatively connected to the scanning system and the conveyor by rotating the rotor at a second, slower rotational rate utilizing the rotator, causing the conveyor to move at a second, faster linear rate, or both;

scanning a second, different object in the second, coarser pitch mode by rotating the rotor at the second, slower rotational rate utilizing the rotator, causing the conveyor to move the second object past the at least one radiation source and the at least one radiation detector at the second, faster linear rate, or both; and while scanning the second, different object, automatically and dynamically causing the scanning system to switch from the second, coarser pitch mode to the first finer pitch mode in response to initial scanning determining that higher resolution image data for the second, different object is necessary to determine the second, different object's contents.

16. The method of claim 15, wherein the scanning system is one of many scanning systems in an assembly of the scanning systems and further comprising automatically and dynamically assigning the scanning system from a first group of scanning systems operating in the first, finer pitch mode to a second group of scanning systems operating in the second, coarser pitch mode to increase average scan quality, and to automatically and dynamically assign the scanning system from the second group of scanning systems to the first group of scanning systems to increase throughput.

17. The assembly of claim 14, wherein the conveyor is one of many conveyors in a conveyor system comprising a diverter and further comprising causing the diverter to send another object to the first group of scanning systems to increase scan quality or to send the other object to the second group of scanning systems to increase throughput.

18. The assembly of claim 17, further comprising causing the diverter to send the object to the second group of scanning systems in response to place of origin, final destination, or owner identity indicating that dangerous items are more likely to be encountered.

19. Non-transitory computer-readable media including computer-executable instructions, which when executed cause a control system for a scanning system to:

scan a first object in a first, finer pitch mode utilizing a scanning system configured to perform computed tomography scanning by rotating a rotor supporting at least one radiation source and at least one radiation detector rotatable with the rotor relative to a stator at a first rotational rate utilizing a rotator operatively connected to the rotor and causing a conveyor extending through the rotor of the scanning system to move the first object past the at least one radiation source and the at least one radiation detector at a first linear rate;

automatically and dynamically cause the scanning system to switch from the first, finer pitch mode to a second, coarser pitch mode by rotating the rotor at a second, slower rotational rate utilizing the rotator, causing the conveyor to move at a second, faster linear rate, or both;

scan a second, different object in the second, coarser pitch mode by rotating the rotor at the second, slower rotational rate utilizing the rotator, causing the conveyor to move the second object past the at least one radiation source and the at least one radiation detector at the second, faster linear rate, or both; and while scanning the second, different object, automatically and dynamically cause the scanning system to switch from the second, coarser pitch mode to the first finer pitch mode in response to initial scanning determining that higher resolution image data for the second, different object is necessary to determine the second, different object's contents.

* * * * *